United States Patent [19]

Krespan

[11] 4,235,804
[45] Nov. 25, 1980

[54] PREPARATION OF PERFLUOROALLYL FLUOROSULFATE

[75] Inventor: Carl G. Krespan, Wilmington, Del.

[73] Assignee: E. I. Du Pont de Nemours and Company, Wilmington, Del.

[21] Appl. No.: 68,080

[22] Filed: Aug. 20, 1979

Related U.S. Application Data

[63] Continuation-in-part of Ser. No. 931,904, Aug. 8, 1978, abandoned.

[51] Int. Cl.$^3$ ............................................. C07C 141/10
[52] U.S. Cl. ........................... 260/458 F; 260/23 XA; 260/543 R
[58] Field of Search .......................... 260/456 F, 458 F

[56] References Cited

U.S. PATENT DOCUMENTS 2,852,554  9/1958  England .............................. 260/481

OTHER PUBLICATIONS

England et al., JACS, 82, 6181 (1960).
Belaventsev et al., Izv. Akad. Nauk Sssr, Ser. Khim., No. 11, pp. 2510–2516 (1972).

*Primary Examiner*—Nicky Chan

[57] ABSTRACT

Perfluoroallyl fluorosulfate is prepared by reacting hexafluoropropene with sulfur trioxide in the presence of boric oxide, boron trichloride, boron trifluoride tri(-lower alkyl) borate, boron oxychloride or boron oxyfluoride.

11 Claims, No Drawings

PREPARATION OF PERFLUOROALLYL FLUOROSULFATE

CROSS-REFERENCE TO RELATED APPLICATION

This is a continuation in part of copending application Ser. No. 931,904, filed Aug. 8, 1978, now abandoned.

TECHNICAL FIELD

This invention relates to the preparation of perfluoroallyl fluorosulfate, and more particularly to the reaction of hexafluoropropene with sulfur trioxide in the presence of a boron catalyst.

BACKGROUND ART

In U.S. Pat. No. 2,852,554, D. C. England discloses the reaction of hexafluoropropene with freshly distilled, liquid, anhydrous sulfur trioxide to obtain 2-hydroxy-1-trifluoromethyl-1,2,2-trifluoroethanesulfonic acid sultone (hexafluoropropene sultone) of the formula

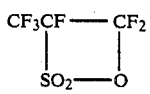

D. C. England, M. A. Dietrich and R. V. Lindsey in "Reaction of Fluoroolefins with $SO_3$", J. Amer. Chem. Soc., 82, 6181 (1960) also report the reaction of hexafluoropropene (HFP) with freshly distilled sulfur trioxide ($SO_3$) at 100° C. to give the sultone of HFP

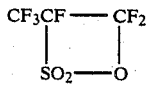

This reference (p. 6184) also reports the reaction of hexafluoropropene with inhibited $SO_3$ at 60° C. to give an unidentified mixture, b.p. 50°–65° C., and a high-boiling product which presumably is a cyclic sulfonate-sulfate anhydride of the formula

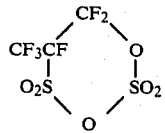

M. A. Belaventsev, L. L. Mikheev, V. M. Pavlov, G. A. Sokol'skii and I. L. Knunyants, Izv. Akad, Nauk SSSR, Ser. Khim. 1972 (11), 2510-16 (Russ), Eng. Trans. 2441-2445, disclose the reaction of $(CF_3)_2C=CF_2$ with $SO_3$ at 150°–180° C. to give

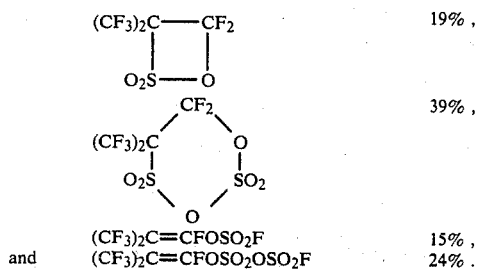

DISCLOSURE OF INVENTION

The present invention is based on the discovery that perfluoroallyl fluorosulfate ($FSO_2OCF_2CF=CF_2$) can be prepared by reacting hexafluoropropene ($CF_3 \times CF=CF_2$) with sulfur trioxide ($SO_3$) under anhydrous conditions in the presence of about 0.1 to about 5% by weight, based on the sulfur trioxide, of a trivalent boron compound selected from the group consisting of boric oxide ($B_2O_3$); boron trichloride ($BCl_3$); boron trifluoride ($BF_3$); tri(lower alkyl) borates ($B(OR)_3$) where the alkyl groups contain 1 to 6 carbons, for example, trimethyl borate and triethyl borate; boron oxychloride (($BOCl)_3$); and boron oxyfluoride (($BOF)_3$) at a temperature of about 0° to about 100° C. for a time sufficient to produce perfluoroallyl fluorosulfate, and recovering perfluoroallyl fluorosulfate from the reaction mixture. The process can also produce varying amounts of the novel tetrafluoropropenyl-1,3-bis(-fluorosulfate) $FSO_2OCF_2CF=CFOSO_2F$ depending on the amount of sulfur trioxide present.

The sulfur trioxide used in this process can be commercial, liquid sulfur trioxide, or it can be freshly distilled, uninhibited sulfur trioxide. Commercial, liquid sulfur trioxide (mp ~17° C.) is sold in sealed glass ampoules and contains a "stabilizer" which inhibits the formation of solid, polymeric sulfur trioxide. Although this material contains a mixture of oligomers (mostly γ-$SO_3$, the cyclic trimer), it remains liquid. The long chain polymer (solid matter) formed in the absence of inhibitor can be cracked back to liquid form, for example by heating at 60° C. Water promotes the formation of solid polymer in the presence of inhibitor. For use in the present invention the $SO_3$ should preferably be liquid at 20° C.

The mole ratio of hexafluoropropene to sulfur trioxide can vary widely. Actually the desired product is obtained even in the presence of a large excess of hexafluoropropene, for example at mole ratios as high as about 100:1. Preferably the mole ratio is about 5:1 to about 1:2. When the ratio is above about 1:1, the major product will tend to be perfluoroallyl fluorosulfate. When the ratio is below about 1:1, the major product will tend to be tetrafluoropropenyl-1,3-bis(fluorosulfate) with minor amounts of perfluoroallyl fluorosulfate.

The boron catalyst is added in the amount of about 0.1 to about 5% by weight relative to the sulfur trioxide and preferably about 0.3 to about 2.8% by weight. The preferred catalysts are $B_2O_3$, $BF_3$, and $B(OCH_3)_3$ because of their high efficiency and availability.

The general procedure for preparing perfluoroallyl fluorosulfate involves addition of sulfur trioxide to a dry, heavy-walled glass tube or a metal tube having a corrosion-resistant liner such as a nickel alloy or stainless steel. Catalyst is added and hexafluoropropene is either pressured in or condensed in. The reaction vessel is sealed and reaction carried out at temperatures from about 0° to about 100° C. (preferably about 25° to about 75° C.) under autogenous pressure for from about one hour to about one week. Inert diluents may be used, but they offer no special advantage. Agitation is desirable but not essential. Protic materials such as water, hydrogen chloride, fluorosulfonic acid, methanol, etc. are deleterious to the reaction and should be avoided.

The time of reaction depends inversely on temperature. Although lower temperatures require a greater time for maximum yield, they favor perfluoroallyl fluorosulfate as product over hexafluoropropene sultone. Higher temperatures tend to decrease yields of perfluoroallyl fluorosulfate and increase the hexafluoropropene sultone content.

Best Mode

The process of this invention is illustrated by the following examples. All temperatures are in degrees Celsius.

EXAMPLE 1

Each of four Carius tubes (150 ml capacity) was charged with 10 ml (19 g) of sulfur trioxide (stabilized with dimethyl phthalate) and 12 drops (0.12 g) of trimethyl borate, cooled with liquid nitrogen, necked down and evacuated. Hexafluoropropene (45 g) was condensed into each tube which was then sealed and warmed to melt and mix the contents. They were heated for 14 hrs. in a water bath at 55°–60°. Analysis of the product by gas chromatography (gc) indicated that the major product was perfluoroallyl fluorosulfate (FAFS). The combined product of the four tubes was fractionally distilled to give 45 g, b.p. mostly 45°, analyzing by gc 75% 2-hydroxy-1-trifluoromethyl-1,2,2-trifluoroethanesulfonic acid sultone (HFPS) and 25% FAFS; 80 g, b.p. mostly 62°, analyzing by gc 95% FAFS; and 44 g of high-boiler not characterized. Based on $SO_3$ charged, the total yield of HFPS was 14.8% and of FAFS 39.6%.

For comparison, the above experiment was repeated except that no trimethyl borate catalyst was added. Analysis of the product by gc indicated that the major product was HFPS and no FAFS was detected.

EXAMPLE 2

The following reactions in which distilled $SO_3$ was employed were carried out in 1200-ml Hastalloy-lined metal tubes. Yields quoted are for product isolated by conventional distillation techniques. The results are summarized in the following table.

were vented. Liquid products were collected and fractionated in a spinning band still to afford 61.3 g (9%) of crude sultone, b.p. 46°–60°; 146.9 g (21%) of perfluoroallyl fluorosulfate, b.p. 60° (1 atm) −44° (350 mm); and 155.4 g of high boiling mixture, b.p. 49°–56° (50 mm). Analysis of the mixture by $^{19}F$ NMR indicated a three-component mixture 82.9 g (18%) of tetrafluoropropenyl-1,3-bis(fluorosulfate), 56.8 g (12%) of 2:1 sultone

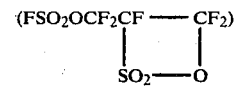

and 15.7 g of $FSO_2OSO_2OSO_2F$.

A center cut of the above high-boiling fraction (64.6 g) was added to 150 ml of diethyl ether at 5°, and the mixture was stirred overnight at room temperature. Fractionation afforded 36.0 g of pure $FSO_2OCF_2CF=CFOSO_2F$, b.p. 54°–55° (50 mm). IR ($CCl_4$): 5.67 (C=C) and 6.72μ($OSO_2F$). $^{19}F$ NMR fit a 1:1.3 mixture of cis/trans isomers of $FSO_2OCF_2CF_2=CFOSO_2F$.

Anal. Calcd. for $C_3F_6O_6S_2$: F, 36.76: Found: F, 36.74.

Industrial Applicability

The ability of boron compounds to catalyze the synthesis of perfluoroallyl fluorosulfate is useful since perfluoroallyl fluorosulfate is disclosed by D. C. England in copending application Ser. No. 931,905, filed Aug. 8, 1978, as being useful in the formation of homopolymers and copolymers with various fluoroethylenes such as vinylidene fluoride, vinyl fluoride, trifluoroethylene, chlorotrifluoroethylene, and tetrafluoroethylene. Particularly preferred copolymers are those of vinylidene fluoride and perfluoroallyl fluorosulfate. Generally the copolymer will contain from about 1 to about 80 and preferably about 5 to about 50 weight percent of the perfluoroallyl fluorosulfate with a fluoroethylene comprising the remainder of the copolymer. The polymers

TABLE I

| $SO_3$ (moles) | $CF_3CF=CF_2$ (moles) | Catalyst (g) | Temp. and Time | $CF_2=CFCF_2OSO_2F$ (% yield) | $CF_3CF-CF_2$ $\mid$ $\mid$ $SO_2-O$ (% yield) |
|---|---|---|---|---|---|
| 3.1[a] | 3.5 | None | 60°/22 hr; then 100°/2 hr | 0 | 86 |
| 2.7 | 3.5 | 1.0 $B(OCH_3)_3$ | 25°/3 days; then 100°/8 hr | 44 | 13 |
| 2.0 | 3.5 | 0.7 $B(OCH_3)_3$ | 25°/5 days; 60°/8 hr; then 100°/2 hr | 60 | 10 |
| 2.1 | 3.5 | 2 $BF_3$ | 25°/5 days; 60°/8 hr; then 100°/2 hr | 60 | 5 |
| 2.1 | 3.5 | 0.5 $B_2O_3$ | 60°/22 hr; then 100°/2 hr | 25 | 42 |

[a]The distilled $SO_3$ was chilled at 0° until it solidified to trimer, m.p. 17°, then melted at 25° to the normal state prior to reaction.

EXAMPLE 3

A 1200-ml Hastalloy-lined tube charged with 240 g (3.0 mol) of $SO_3$, 3 g of $BF_3$, and 525 g (3.5 mol) of hexafluoropropene was agitated briefly, then allowed to stand at 25° C. for 3 days. After having been heated at 100° C. for 8 hr, the tube was cooled at 0° C. while gases find use as ion exchange resins and as acid catalysts.

The tetrafluoropropenyl-1,3-bis(fluorosulfate) is useful as an intermediate in the formation of

which is useful in the preparation of carboxylated fluoropolymers which find use as chloralkali cell membranes and diaphragms. The bis(fluorosulfate) is chlorinated or fluorinated in accordance with the equation:
$FSO_2OCF_2CF=CFOSO_2F+X_2 \rightarrow FSO_2OCF_2CFXCFXOSO_2F$. This product is then treated with a basic catalyst such as pyridine or KF as reported by I. L. Knunyants and G. A. Sokolski, Angew, Chem. internat. Edit., 11, 586 (1972) to form

This is then reacted with KF and perfluoroallyl fluorosulfate to form the desired monomer.

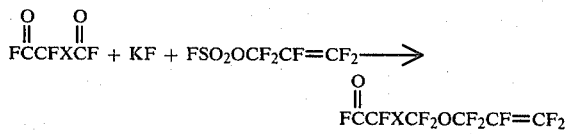

I claim:

1. Method of preparing perfluoroallyl fluorosulfate which comprises reacting hexafluoropropene with sulfur trioxide in a mole ratio of 100:1 to 1:2 under anhydrous conditions in the presence of 0.1 to 5% by weight, based on the sulfur trioxide, of a trivalent boron compound selected from the group consisting of boric oxide, boron trichloride, boron trifluoride, tri(lower alkyl) borates where the alkyl groups contain 1 to 6 carbon atoms, boron oxychloride and boron oxyfluoride at a temperature of 0° to 100° C. for a time sufficient to produce perfluoroallyl fluorosulfate, and recovering perfluoroallyl fluorosulfate from the reaction mixture.

2. The method of claim 1 in which the mole ratio of hexafluoropropene to sulfur trioxide is in the range of 5:1 to 1:2.

3. The method of claim 2 in which the mole ratio is in the range of 5:1 to 1:1.

4. The method of claim 3 in which the catalyst is boric oxide.

5. The method of claim 3 in which the catalyst is boron trifluoride.

6. The method of claim 3 in which the catalyst is trimethyl borate.

7. The method of claim 3 in which the temperature is 25°–75° C.

8. The method of claim 7 in which the reaction is carried out under autogeneous pressure.

9. The method of claim 8 in which the catalyst is boric oxide.

10. The method of claim 8 in which the catalyst is boron trifluoride.

11. The method of claim 8 in which the catalyst is trimethyl borate.

* * * * *